(12) United States Patent
Faucher

(10) Patent No.: US 8,507,571 B2
(45) Date of Patent: Aug. 13, 2013

(54) MACRO-PHOTOINITIATOR VIA ENZYMATIC POLYMERIZATION

(75) Inventor: Santiago Faucher, Oakville (CA)

(73) Assignee: Xerox Corporation, Norwalk, CT (US)

( * ) Notice: Subject to any disclaimer, the term of this patent is extended or adjusted under 35 U.S.C. 154(b) by 670 days.

(21) Appl. No.: 12/629,583

(22) Filed: Dec. 2, 2009

(65) Prior Publication Data

US 2011/0130481 A1    Jun. 2, 2011

(51) Int. Cl.
  *B41J 2/16*    (2006.01)
  *C08G 8/02*    (2006.01)
  *C12P 7/62*    (2006.01)

(52) U.S. Cl.
  USPC ............... 522/35; 522/42; 522/130; 522/144; 522/182; 528/128; 435/135

(58) Field of Classification Search
  USPC ............ 522/35, 42, 130, 144, 182; 528/128; 435/135
  See application file for complete search history.

(56) References Cited

U.S. PATENT DOCUMENTS

| | | | |
|---|---|---|---|
| 4,442,022 A | 4/1984 | Van der Hauw et al. | |
| 5,147,791 A | 9/1992 | Morrow et al. | |
| 5,486,444 A | 1/1996 | Bayley et al. | |
| 5,527,925 A | 6/1996 | Chabrecek et al. | |
| 5,643,356 A | 7/1997 | Nohr et al. | |
| 5,859,084 A | 1/1999 | Schröder et al. | |
| 5,981,743 A | 11/1999 | Gross et al. | |
| 6,011,077 A | 1/2000 | Müller | |
| 6,031,044 A | 2/2000 | Kokel et al. | |
| 6,248,804 B1 | 6/2001 | Lutz | |
| 6,296,986 B1 | 10/2001 | Illsley et al. | |
| 6,596,786 B2 | 7/2003 | Purvis et al. | |
| 6,972,315 B2 | 12/2005 | Gross et al. | |
| 7,166,649 B2 | 1/2007 | Day et al. | |
| 7,271,284 B2 | 9/2007 | Toma et al. | |
| 2004/0242831 A1 | 12/2004 | Tian et al. | |
| 2006/0286570 A1* | 12/2006 | Rowlen et al. | 435/6 |
| 2007/0123723 A1 | 5/2007 | Odell et al. | |
| 2010/0120938 A1* | 5/2010 | Phelan et al. | 523/107 |

OTHER PUBLICATIONS

Varma et al., "Enzyme Catalyzed Synthesis of Polyesters", Prog. Polym. Sci. 30 (2005), pp. 949-981.
Takwa et al., "Single-Step, Solvent-Free Enzymatic Route to α,ω-Functionalized Polypentadecalactone Macromonomers", Macromolecules, 2008, 41, pp. 5230-5236.
U.S. Appl. No. 12/240,421.

* cited by examiner

*Primary Examiner* — Michael Pepitone
*Assistant Examiner* — Jessica Roswell
(74) *Attorney, Agent, or Firm* — Oliff & Berridge, PLC

(57) ABSTRACT

Disclosed herein is a macro-photoinitiator comprising a photoinitiator covalently bound to a polymer. Also disclosed herein is a process for the enzymatic polymerization of monomers and photoinitiators performed at atmospheric pressure and relatively low temperatures to form the macro-photoinitiator.

17 Claims, 8 Drawing Sheets

MACRO-PHOTOINITIATOR VIA ENZYMATIC POLYMERIZATION

BACKGROUND

Disclosed herein is a macro-photoinitiator comprising a photoinitiator covalently bound to a polymer. Also disclosed herein is a low temperature process for the enzymatic polymerization of monomers.

Polyester-based compositions, including low-melt polyester compositions, frequently include photoinitiators that aid in curing of the composition after printing or application to a substrate. However, photoinitiators can migrate or leach from polyester-based compositions such as coatings and toners, both before and after curing. This causes undesirable effects such as (1) discoloration of the composition, (2) loss of adhesion to the substrate, (3) incomplete cure and the like. Additionally, incorporation by blending of photoinitiators into polyester compositions can affect the rheology and glass transition temperature (Tg) properties of the polyester-based compositions prior to curing.

Low-melt polyester-based toners and inks use a combination of amorphous and crystalline polyesters to achieve low-melt behavior, enabling faster print speeds and lower energy consumption. While the melting behavior of polyester-based toners provides advantages over polystyrene-based chemical toners in print speed, fuser life and energy consumption, the synthesis of the polyester resin is time and energy-consuming. In particular, the preparation of polyesters by polycondensation takes several days and relies on high temperatures (T≧190° C.) and low pressures (p≦10 mmHg) to drive the polymerization to completion. Condensation polymerizations also utilize metal based catalysts that are difficult to completely remove from polyester products. These metals reduce the biodegradability of polyesters and so are not desirable.

An additional difficulty with conventional preparation of polyesters by polycondensation is the high temperatures (T≧190° C.) required for preparing polyesters in a polycondensation processes. These high temperatures degrade photoinitiators, and thereby decrease or entirely destroy the reactivity (and thus the effectiveness) of any photoinitiator added.

For example, IRGACURE 2959 is a conventional small molecule photoinitiator available from CIBA Specialty Chemicals used in curing compositions. FIG. 1 is a graph showing the decrease in functionality of IRGACURE 2529 as a function of temperature. As shown in FIG. 1, the degradation of IRGACURE 2529 begins as low as 125° C. and proceeds rapidly to complete degradation as temperature increases above 200° C. During the polycondensation reaction, which regularly takes up to ½ day to complete, a large fraction of the photoinitiator will be degraded.

What is desired is a photoinitiator that is easy to disperse into polymeric materials, forms a stable dispersion in polymeric materials, does not leach out of compositions to which it is added and does not affect the Tg or rheology of polymeric materials to which it is added. Further desired is a low-cost enzymatic polymerization process that eliminates the need for the use of metal based catalysts to enable production of metal-catalyst free polyesters.

SUMMARY

At least the above objects are achieved herein. In embodiments, described is a process for producing a macro-photoinitiator via enzymatic polymerization, the process comprising providing a reaction solution comprised of at least one monomer and at least one reactive photoinitiator having at least one reactive moiety reactive with the at least one monomer, contacting the reaction solution with at least one enzymatic catalyst, and heating to enzymatically polymerize the at least one monomer and form a polymeric product solution comprised of a macro-photoinitiator, wherein the macro-photoinitiator has the at least one reactive moiety of the at least one photoinitiator covalently bound to a polymer moiety formed from the at least one monomer.

In embodiments, also described is a macro-photoinitiator having a formula photoinitiator-R—O-polymer, wherein R is a straight or branched carbon atom chain, saturated or unsaturated, having from 1 to 30 carbon atoms and optionally with one or more carbon atoms substituted with a heteroatom.

In embodiments, further described is a curable composition comprising at least one UV curable matrix material and at least one macro-photoinitiator.

EMBODIMENTS

Figure 1:
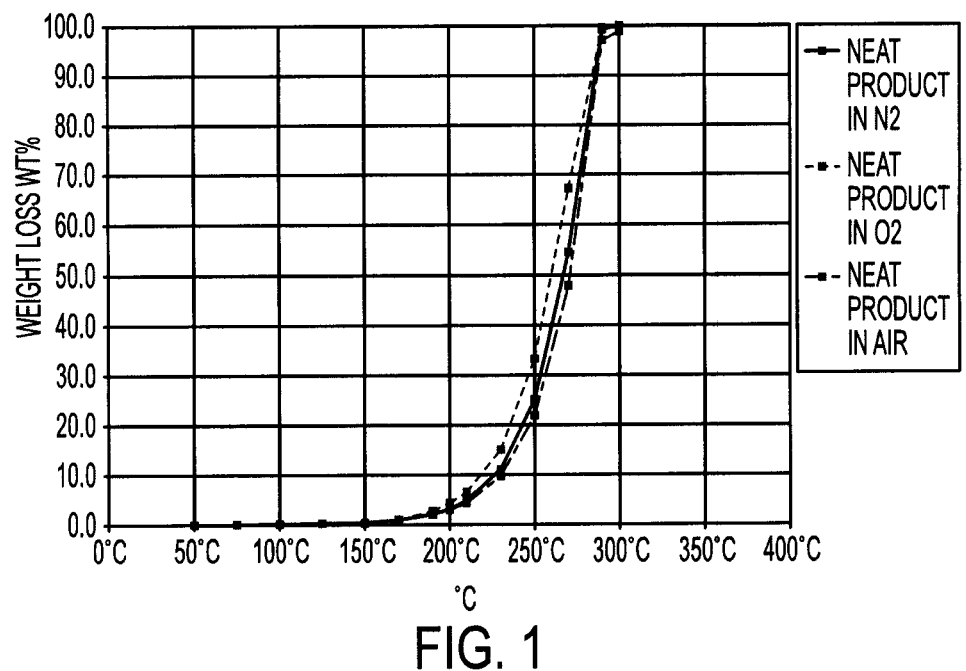
FIG. 1 is a graph depicting loss of functionality of IRGACURE 2529 photoinitiator as a function of increased temperature.

As used herein, "macro-photoinitiator" refers to a photoinitiator covalently bound with a polymer.

The present application includes a process for the enzymatic polymerization of monomers with photoinitiator small molecules performed at atmospheric pressure and relatively low temperatures, such as, for example, from about 40° C. to about 100° C., or from about 50° C. to about 90° C., or from about 60° C. to about 80° C. As such, the enzymatic polymerization may be accomplished at a lower temperature and without significant, or without any, degradation of the photoinitiator. The resulting macro-photoinitiator thus retains high activity for photoinitiation.

The above polymerization is accomplished by providing a reaction solution including at least one reactive photoinitiator and at least one reactive monomer, such as an ester-forming monomer, for example a lactone or cyclic ester. The reaction solution may be added to a reactor where the enzymatic polymerization is conducted to form the macro-photoinitiator comprising a photoinitiator bound to a polymer derived from the reactive monomer.

Photoinitiators

The macro-photoinitiator is a photoinitiator covalently bound to a polymer, such as a polyester, through enzymatic reaction of monomers such as lactones or similar cyclic esters. In embodiments, the photoinitiator may be bound at the α-position or terminal portion on the formed polymer.

Photoinitiators are used to induce polymerization of ethylenically unsaturated monomeric, oligomeric or polymeric compounds. When exposed to radiation, such as UV-light radiation, or infrared (IR) radiation, a photoinitiator homolytically cleaves to form radical species capable of initiating free radical polymerization of vinyl monomers or of cross-linking groups in unsaturated polymers, such as polyesters, polyurethanes or polyethers.

Covalent bonding of the photoinitiator to a polymer forms a macro-photoinitiator which does not increase the number of free chain ends of the polymer, and thereby reduces the potential for alteration of the glass transition temperature (Tg) or rheology characteristics of a polymer comprising a photoinitiator as compared to polymers blended with conventional small molecule photoinitiators. Small molecule photoinitiators are known to plasticize polymers and thus change their thermal (glass transition (Tg)) and rheological behavior. The covalent bond between the photoinitiator and the polymer increases the functional molecular size of the photoinitiator, and thereby reduces the ability for the photoinitiator to phase separate out of a matrix (for example, comprised of a polymer to be cured) within which it is dispersed. Additionally, the diffusivity of the photoinitiator is greatly inhibited by its bonding to a macromolecule (polymer), such as a polyester, that is readily incorporated in the matrix. Thus, the covalent bonding of the photoinitiator reduces the ability of the photoinitiator to phase separate out of the polymer matrix, at least by facilitating dispersion of the bound photoinitiator in the polymer matrix. In contrast, small molecules such as conventional photoinitiators tend to diffuse out of the matrix as oily materials that can potentially adversely affect the functional properties of the material, such as curing performance.

The photoinitiator must be reactive with a monomer species while still retaining photoinitiator functionality even after reaction. This may be achieved with a photoinitiator having at least one reactive end group. An example of a reactive group of a photoinitiator is a reactive hydroxyl group. Thus, any photoinitiator with a reactive group, in particular a reactive hydroxyl group, may be used. For example, any photoinitiator that can be utilized as an initiator for the enzymatic polymerization of lactones or other ester-forming monomers is suitable, so long as the primary reactive group, such as hydroxyl, is attached to the photoinitiating moiety through an aliphatic chain. The photoinitiator may thus have the formula:

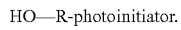

HO—R-photoinitiator.

The formula represents the structure of a suitable initiator for production of macro-photoinitiators via enzymatic polymerization, where R is an aliphatic chain tethering the primary alcohol to a photoinitiator moiety that does not prevent the photoinitiator from homolytically cleaving under UV-light irradiation. As the aliphatic chain R, any straight or branched carbon atom chain, saturated or unsaturated, may be used. In addition, one or more carbon atoms may be substituted with a heteroatom such as sulfur, nitrogen and the like. The aliphatic chain may have a size of from, for example, 1 to 30, such as 1 to 20 or 4 to 20, carbon atoms.

An example of a suitable photoinitiator is 1-[4-(2-hydroxyethoxy)-phenyl]-2-hydroxy-2-methyl-1-propane-1-one (available as IRGACURE 2529, from CIBA Specialty Chemicals) having the below chemical formula. Additional photoinitiators may be any commercially available photoinitiators including OH groups or photoinitiators modified to include reactive OH groups.

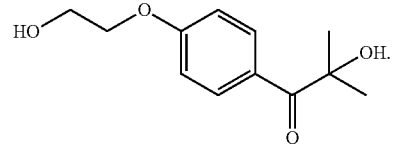

IRGACURE 2529

Monomers

In embodiments, the reaction solution for forming the macro-photoinitiator includes at least one monomer. The monomer may be an ester-forming monomer. Lactone monomers are a suitable example. In embodiments, the monomer may be a cyclic or a non-cyclic straight or branched chain monomer. As cyclic monomers, any appropriate cyclic monomer may be used in the enzymatic ring-opening polymerization, such as a cyclic ester having from about 5 to about 25 carbon atoms, such as about 6 to about 20 carbon atoms, about 7 to about 16 carbon atoms, or about 8 to about 12 carbon atoms. Examples of appropriate monomers include substituted or unsubstituted monomers such as oxacycloheptadec-10-en-2-one (available as AMBRETTOLIDE, from Penta Manufacturing Co.), pentadecalactone, 11/12-pentadecen-15-olide (also known as pentadecenlactone), hexadecenlactone, caprolactone, cyclic diester lactide, butyrolactone, propyl malolactone, propiolactone, 1,4-dioxan-2-one, valerolactone, mixtures thereof and the like. Additional examples of suitable monomers may be found in Varma et al., Enzyme Catalyzed Synthesis of Polyesters, Prog. Polym. Sci., 30 (2005), pgs. 949-981.

The molar ratio of photoinitiator to monomer in the reaction solution may be any effective molar ratio, such as about 200:1, about 30:1, about 20:1, about 10:1, or about 5:1 photoinitiator:monomer. Variation in concentration of photoinitiator to cyclic monomer can be used to control the molecular weight of the polymeric product.

Optional Additional Additives

The monomer may be provided to the reaction solution independently, or in the form of a monomer solution comprising monomer and a solvent.

The reaction solution may thus also comprise one or more suitable solvents, such as toluene, benzene, hexane and its analogs (such as heptane), and tetrahydrofuran and its analogs (such as 2-methyltetrahydrofuran), and methyl ethyl ketone and its analogs.

The solvent may be mixed with the monomer prior to or after addition of the monomer to the reaction solution. When present, the solvent may be of any appropriate concentration range relative to the content of monomer. For example, the solvent may comprise from 1% to about 99% of the total weight of the solvent and the cyclic monomer, such as from about 10% to about 90%, such as from about 25% to about 75%, such as from about 40% to about 60%, or such as about 50% of the total weight of the solvent and the monomer.

Enzymes

The reaction solution may further include one or more enzymes, such as a lipase. The one or more enzymes assist to catalyze the reaction of the photoinitiator and the monomer, and allow the polymerization to occur at low temperatures. For example, the lipase may be lipase PA, lipase PC, lipase PF, lipase A, lipase CA, lipase B (such as *candita antartica* lipase B), lipase CC, lipase K, lipase MM, cutinase or porcine lipase.

The enzymes may be present in the reaction solution in immobilized or free form. As used herein, the term "immobilized enzyme" is synonymous and used interchangeably with "supported enzyme", and includes enzymes that are supported but not immobilized (such as enzymes that are adsorbed to a polymeric support non-covalently); enzymes that are immobilized but not supported, such as enzymes that are cross-linked to other enzymes; and enzymes that are both supported and immobilized.

Initiators

The reaction solution may further comprise one or more polymerization initiators, in addition to the photoinitiator. The initiator may be water or an additional molecule comprising one or more reactive groups such as hydroxyl groups. Polymerization initiators differ from the photoinitiator in that they merely facilitate initiation of polymerization of the monomer, but are not themselves photoinitiators that assist in subsequent curing of a polymer. Thus, the additional initiators facilitate production of polymers as opposed to macro-photoinitiators.

In embodiments, if present in the reaction solution, water may polymerize additional monomer that does not react with the photoinitiator. As such, the polymeric product solution may comprise a mixture of macro-photoinitiator and polymer formed from the monomer.

Reaction and Conditions

As can be seen in the following reaction diagram ("Reaction Diagram I"), a photoinitiator may be bound to a polyester through enzymatic ring-opening reaction, thereby creating a macro-photoinitiator.

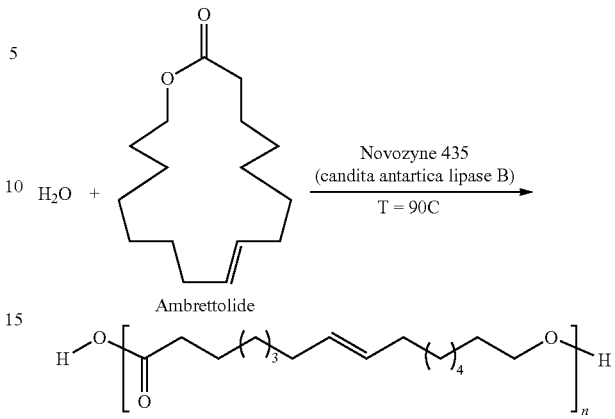

The process is initiated by either water present in the reaction medium or the hydroxyl group on the photoinitiator. Thus, two polymeric populations are created through this mechanism, one with an α-photoinitiator and another with an α-hydroxyl group, the latter of which is not photoactive. The dual population of the polymers does not affect the performance of the material.

The process may be achieved through any appropriate enzymatic polymerization technique. In embodiments, the process may be carried out in bulk or in solution, in either a batch or a continuous reactor configuration. In the processes, the reaction solution of monomer and photoinitiator is con-

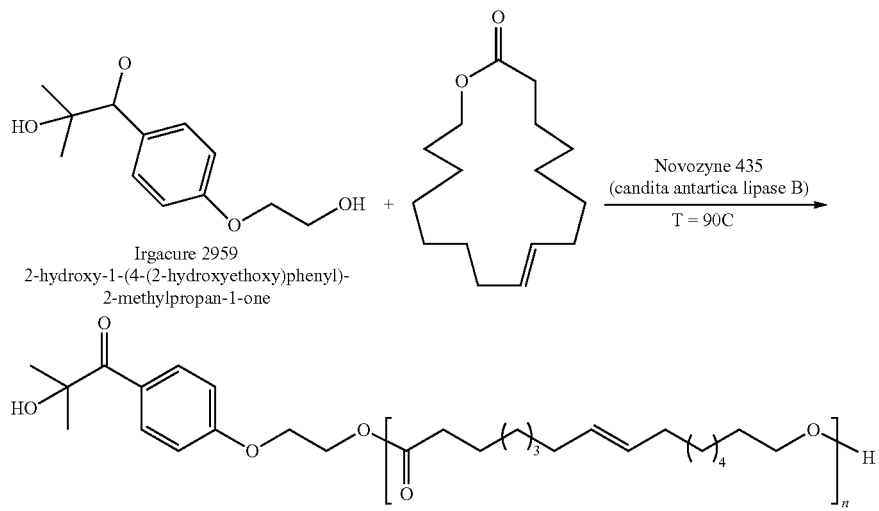

The resulting macro-photoinitiator may be generalized to have a structure photoinitiator-R—O-polymer, where the polymer includes n linked chains of the reactive monomer, n being an integer of polymeric length, such as from 3 to 200 and the like.

As can be seen in the following reaction diagram ("Reaction Diagram II"), cyclic monomer may also be polymerized through ring-opening reaction initiated by water, such as water optionally present in the reaction system.

tacted with the enzyme catalyst, and subjected to heating of, for example, about 40° C. to about 100° C. while in contact with the enzyme catalyst. The contacting may be achieved either by mixing the enzyme catalyst into the reaction solution, or by contacting the reaction solution with a packed bed in which the enzyme catalyst is trapped.

In solution polymerization, an enzyme is packed in a column reactor and monomer is pumped through the enzyme bed to continuously form polymer materials.

Polymerization in a packed-bed reactor includes a reactor having one or more immobilized enzymes, wherein the packed-bed reactor has an inlet and an outlet, and is fed with a solution of cyclic ester monomer and photoinitiator. The method may further include circulating a solution of the monomer and photoinitiator through the packed-bed reactor to generate a solution enriched with macro-photoinitiator, such that the one or more immobilized enzymes convert the one or more monomers and the photoinitiator to macro-photoinitiator in the packed-bed reactor during circulation, and collecting the solution enriched with macro-photoinitiator exiting through the outlet.

In embodiments, the packed-bed reactor may include one or more immobilizing agents for immobilizing the enzyme, such as a cross-linked polymeric network, cross-linked polymeric beads, polymeric packings, membranes, silica-gel, silica beads, sand and zeolites.

In embodiments, the reactor may be made from any appropriate material, such as stainless-steel tubing, glass tubing or polymer tubing (such as polyetheretherketone (PEEK) tubing).

The reactor may have any suitable diameter and length. In embodiments, the reactor can have an outer diameter of from about 0.1 cm to about 300 cm, such as from about 10 cm to about 100 cm, and a length of from about 1 cm to about 300 cm.

In bulk polymerization, the enzyme and the monomer are added to the reaction kettle and stirred.

In both bulk and solution polymerization, photoinitiator is added as an hydroxyl initiating site for the enzymatic polymerization.

Bulk and solution polymerization of polyesters in a continuous packed-bed reactor using immobilized enzyme catalysts is further disclosed in U.S. patent application Ser. No. 12/240,421, which is hereby incorporated herein in its entirety by reference.

In embodiments, the method may also include controlling one or more of molecular weight, polydispersity and conversion ratio of the photoinitiator and monomer to macro-photoinitiator using one or more of residence time of the one or more cyclic esters and photoinitiator in the reactor, dimensions of the reactor, composition of the reactor, temperature of the reactor and initiator concentration in the photoinitiator and monomer solution. In embodiments, decreasing the feed rate of the reaction solution to the reactor may cause the residence time of the reaction solution within the reactor to increase, and this in turn may cause an increase in the conversion to macro-photoinitiator and an increase in the molecular weight of the macro-photoinitiator product.

In embodiments, the process may include monitoring the macro-photoinitiator product solution collected from the outlet of the reactor to monitor the conversion of the photoinitiator and one or more monomers to a photoinitiator-polymer product. In embodiments, the monitoring includes collecting the macro-photoinitiator product solution when the product has attained a substantially stabilized molecular weight or desired molecular weight. In embodiments, the monitoring includes collecting and analyzing the product solution to determine molecular weight of the macro-photoinitiator in the solution. Any suitable technique can be used for the analysis of the macro-photoinitiator in the solution, such as gel permeation chromatography (GPC), differential scanning calorimetry (DSC) and nuclear magnetic resonance (NMR).

Following polymerization, the collected macro-photoinitiator may be precipitated into a solvent, such as methanol, and recovered by filtration to eliminate any residual solvent or monomer. The resulting cake may be extracted via any appropriate extraction, such as soxhlet extraction, in an effort to remove any unreacted photoinitiator and unreacted monomer from the polymer product.

In embodiments, the reactor may provide in-situ filtration because the immobilized catalyst remains in the tube during the reaction, thereby avoiding the additional step of diluting and filtering of the reaction mixture after the polymerization has completed.

Reaction Products

The macro-photoinitiator may be of any appropriate molecular weight, such as from about 2,000 Da $M_w$ to about 140,000 Da $M_w$, from about 5,000 Da $M_w$ to about 100,000 Da $M_w$, or from about 10,000 Da $M_w$ to about 70,000 Da M, as determined by GPC relative to polystyrene standards.

In embodiments, the macro-photoinitiator is a crystalline macro-photoinitiator.

Figure 2:
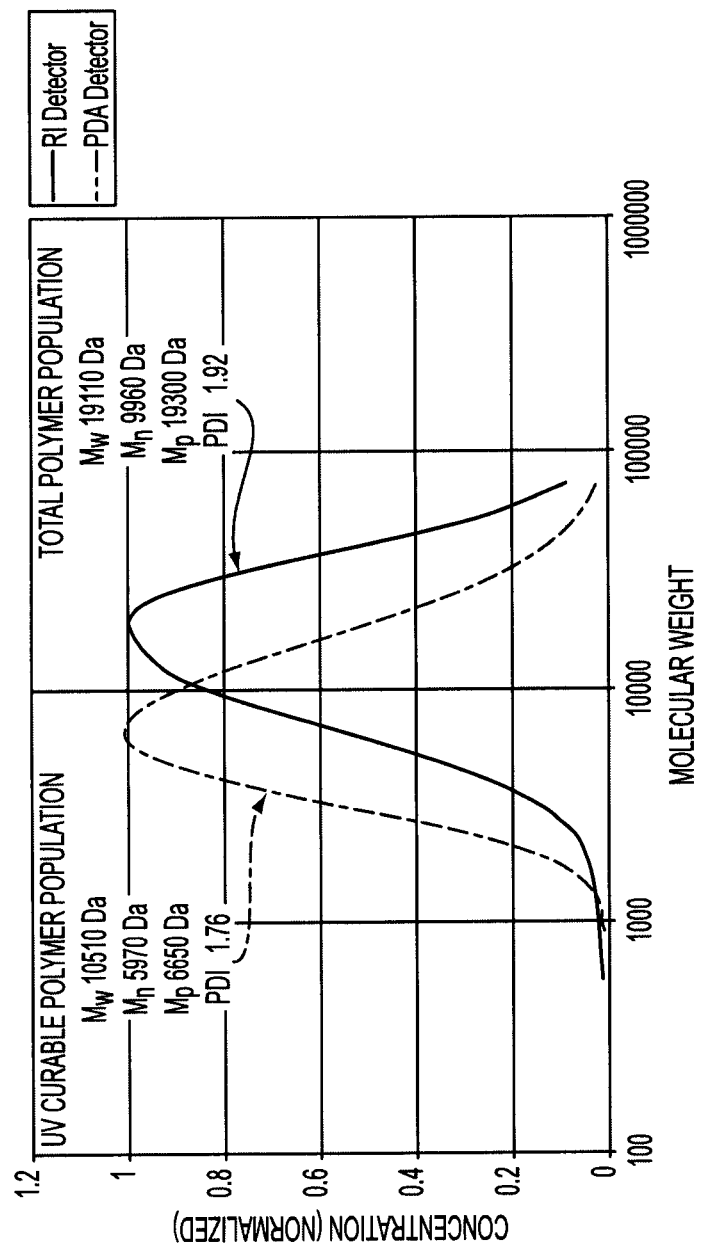
FIG. 2 is a graph depicting gel permeation chromatography (GPC) of a macro-photoinitiator and a polyester using a photo-diode array detector and refractive index detector to confirm binding between a photoinitiator and a polyester polymer.

Confirmation of the covalent binding between the photoinitiator and the formed polymer may be confirmed by photodiode-array detector (PDA) and refractive index detector (RI) analysis. FIG. 2 is a graph depicting gel permeation chromatography of a macro-photoinitiator and a polymer using a photo-diode array detector and refractive index detector to confirm binding between the photoinitiator and the polyester polymer. The total polymer population can be observed by the RI detector signal, while the sub-population containing the macro-photoinitiator is observed by PDA detector.

In embodiments, the macro-photoinitiator may be used to cure or polymerize any curable monomer, macromer, oligomer and/or polymer, including curing or polymerizing the macro-photoinitiators disclosed herein. In embodiments, the macro-photoinitiator may cure reactive acrylate groups on a curable monomer or polymer. Examples of suitable curable monomers, macromers, oligomers, and polymers include SR9003 (propoxylated neopentyl glycol diacrylate, available from Sartomer Co.), styrene, alpha-methylstyrene, substituted styrene, vinyl esters, vinyl ethers, N-vinyl-2-pyrrolidone, (meth)acrylamide, N-substituted (meth)acrylamide, octyl (meth)acrylate, nonylphenol ethoxylate (meth)acrylate, isononyl (meth)acrylate, isobornyl (meth)acrylate, 2-(2-ethoxyethoxy)ethyl (meth)acrylate, 2-ethylhexyl (meth)acrylate, lauryl (meth)acrylate, β-carboxyethyl (meth)acrylate, isobutyl (meth)acrylate, cycloaliphatic epoxide, α-epoxide, 2-hydroxyethyl (meth)acrylate, (meth)acrylonitrile, maleic anhydride, itaconic acid, isodecyl (meth)acrylate, dodecyl (meth)acrylate, n-butyl (meth)acrylate, methyl (meth)acrylate, hexyl (meth)acrylate, (meth)acrylic acid, N-vinylcaprolactam, stearyl (meth)acrylate, hydroxy functional caprolactone ester (meth)acrylate, isooctyl (meth)acrylate, hydroxyethyl (meth)acrylate, hydroxymethyl (meth)acrylate, hydroxypropyl (meth)acrylate, hydroxyisopropyl (meth)acrylate, hydroxybutyl (meth)acrylate, hydroxyisobutyl (meth)acrylate, tetrahydrofurfuryl (meth)acrylate, combinations of these, and the like. In embodiments, the macro-photoinitiator may be used to cure polyester polymers. In embodiments, the macro-photoinitiator may be used to cure the macro-photoinitiators; that is, the macro-photoinitiator may be used to cure the polymer with which it is bound.

The macro-photoinitiator may be mixed with a curable monomer, macromer, oligomer and/or polymer prior to curing. The macro-photoinitiator may be added directly from the solution from which it is prepared, or it may be purified in any recovery procedure prior to adding, such as filtering. The curing may be accomplished by exposing the macro-photoinitiator and any curable monomer, macromer, oligomer and/or polymer mixture to UV-light radiation.

The macro-photoinitiator may comprise the entirety of the curable material, or the macro-photoinitiator may be present in the mixture of macro-photoinitiator and curable monomer, macromer, oligomer and/or polymer in an effective amount, such as from about 0.5% to about 40% by weight of the total mixture, from about 1% to about 30% by weight of the total mixture, from about 2% to about 20% by weight of the total mixture, or from about 5% to about 10% by weight of the total mixture.

The macro-photoinitiator may be used in any suitable curable composition, such as a UV curable paint, a coating, a top coating, a clear coating, ink and the like. The curable compositions thus comprise a curable matrix or binder material comprised of the macro-photoinitiator alone or together with additional curable monomers, oligomers or polymers. Additional additives may also be included in the curable composition, depending on the intended use of the curable composition. For example, inks and coatings may also include one or more colorants such as pigments and dyes.

Curable compositions including the macro-photoinitiator discussed above comprise macro-photoinitiator that advantageously disperses in the matrix of the curable composition without the tendency, or with reduced tendency, of the macro-photoinitiator to leach out of or phase separate from the curable composition, as compared to conventional small molecule photoinitiators in curable compositions. Additionally, curable compositions including a macro-photoinitiator exhibit reduced Tg and/or rheology alteration as compared to curable compositions comprising conventional photoinitiators, for example due to the macro-photoinitiator having a size more closely matched to that of the polymer matrix that is to be cured.

EXAMPLES

Example 1

Reaction Diagram I, above, summarizes the reaction scheme for the Example 1 process. AMBRETTOLIDE (10 g, 0.04 moles), Novozyme 435 catalyst (*Candita Antartica* Lipase B supported on beads, 0.33 g), toluene (10.9 g), and IRGACURE 2959 (0.56 g, 0.0025 moles) were loaded into a 25 mL glass schlenk flask along with a stir bar. The flask was sealed with a rubber septum and then placed in an oil-bath preset to 90° C. for 24 hours. Following this period, the flask was allowed to cool and the contents were recovered. The solid, wax-like material was then dissolved in a small amount of dichloromethane (~30 mL), filtered via vacuum filtration to remove the catalyst, and then the filtrate was added to 300 mL of methanol to precipitate the polymer out of solution. The polymer precipitate was recovered via a second vacuum filtration and the retentate loaded to a soxhlet thimble. The material was then soxhlet extracted in methanol to wash the polymer precipitate over 48 hours so that any unreacted IRGACURE 2959 not chemically bound to the polymer would be washed away. IRGACURE 2959 is highly soluble in methanol while the polymer is not.

Gel Permeation Chromatography (GPC) analysis using a photo-diode array detector (PDA) and a refractive index detector (RI) confirmed that IRGACURE 2959 was tethered to a part of the polymer population. The chromatographs were generated in tetrahydrofuran (THF) using polystyrene standards for both the RI and PDA detectors. The results of this analysis are illustrated in FIG. 2. The results show that a portion of the polymer was polymerized by free water in the reaction system.

Figure 3:
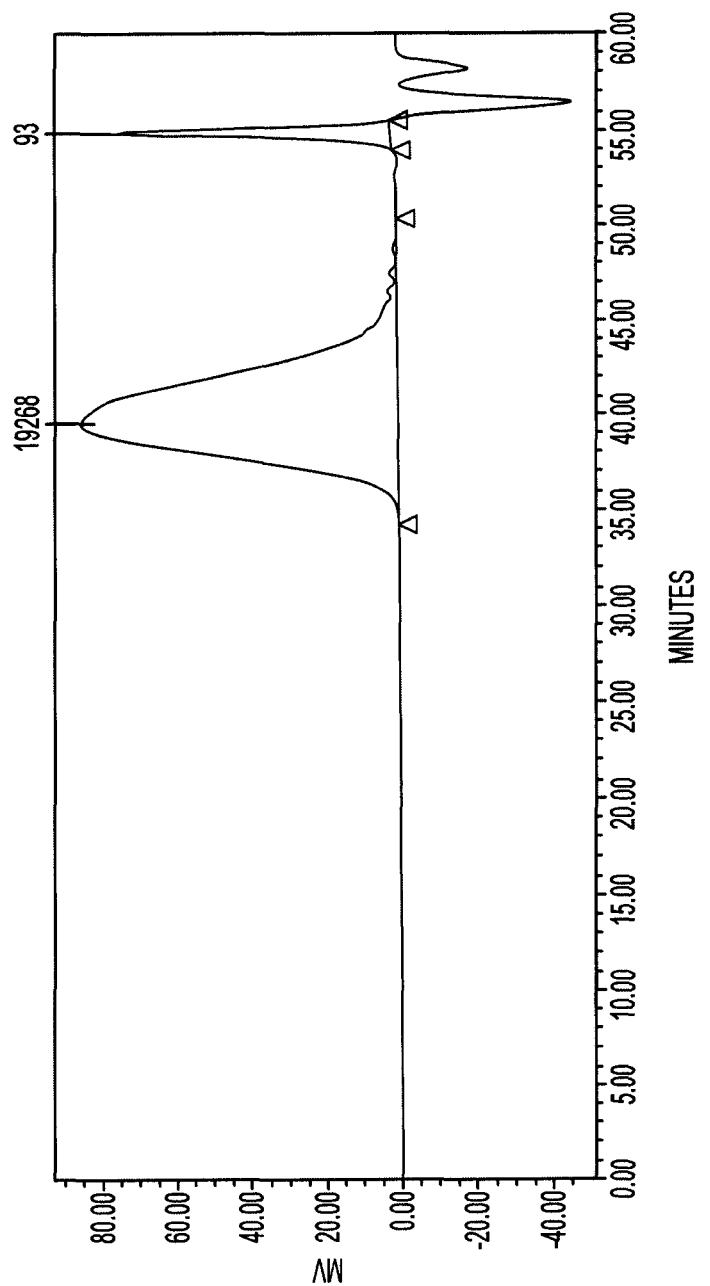
FIG. 3 depicts the GPC analysis results of the reaction product of a photoinitiator and a lactone as tested using a refractive index (RI) detector.

FIG. 3 shows the gel permeation chromatograph generated by the RI detector. Analysis of the chromatogram reveals that the total polymer population has a $M_w$ of 19,110 Daltons (Da), a $M_n$ of 9,960 Da, and a polydispersity (PD) of 1.92. This data is also shown as the solid line in FIG. 3.

Figure 4:
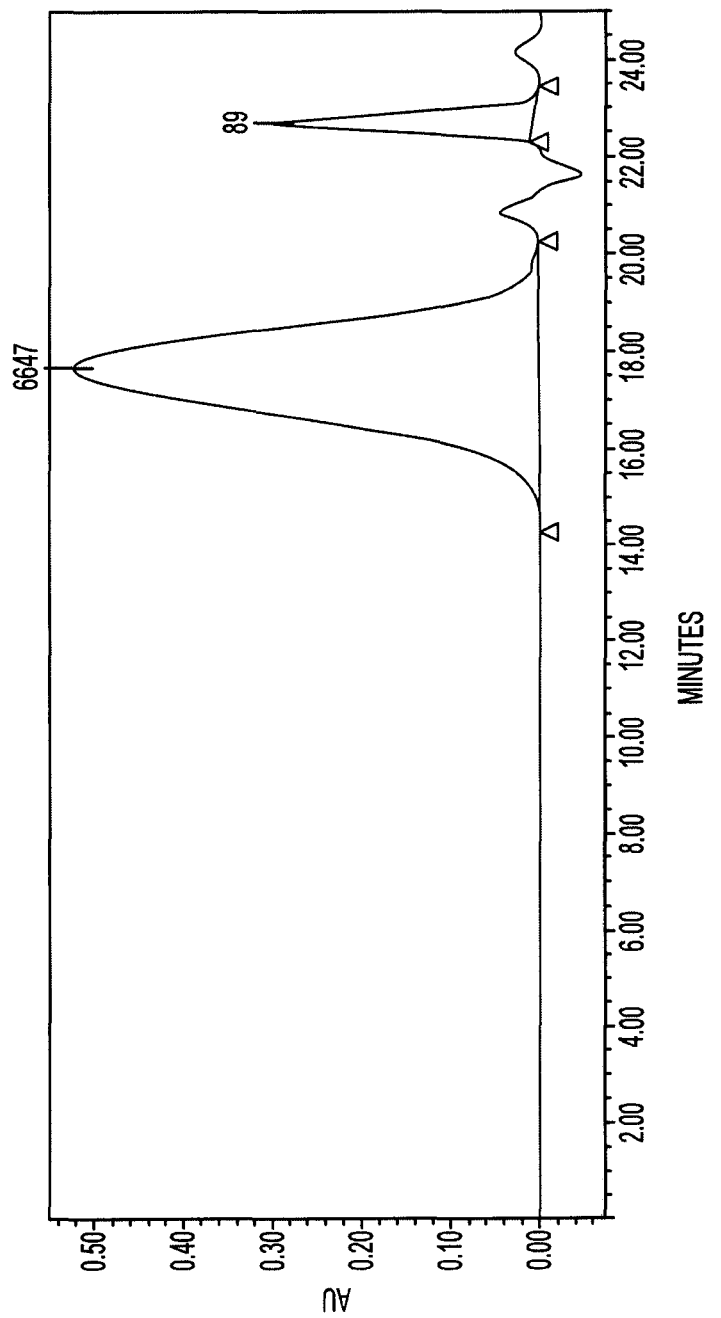
FIG. 4 depicts the GPC analysis results of the reaction product of a photoinitiator and a lactone as tested using a photo-diode array (PDA) detector.

FIG. 4 shows the chromatograph generated by the PDA detector and the UV-visible polymer population (the macro-photoinitiator product). Analysis of this chromatograph shows that this sub-population has a $M_w$ 10,510 Da, a $M_n$ of 5,970 Da, and a PD of 1.76. This data is also shown in the dashed line in FIG. 3.

Figure 5:
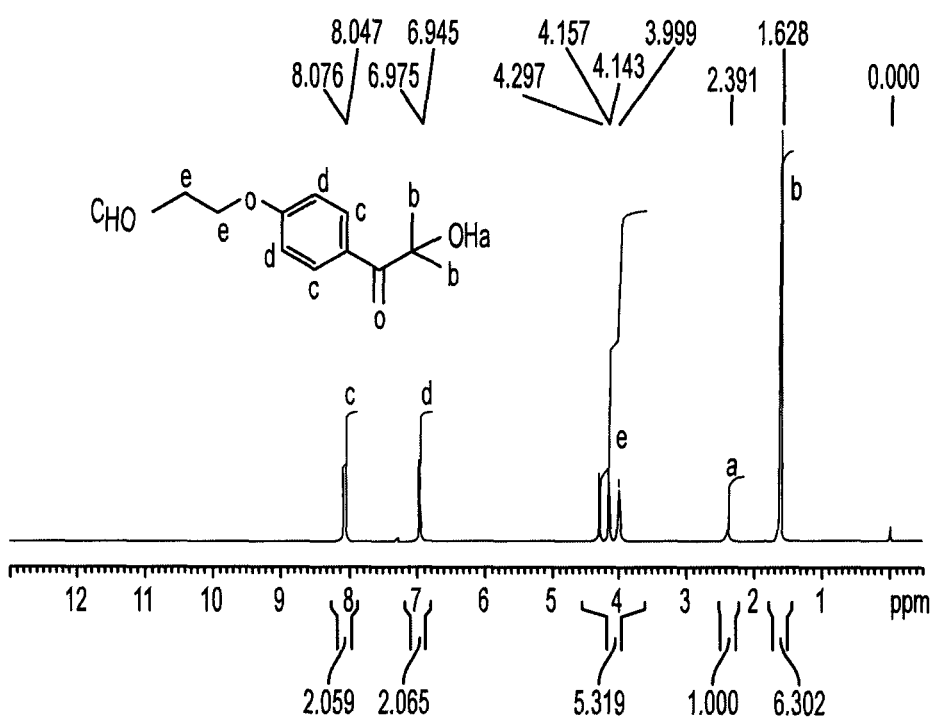
FIG. 5 is a 1H NMR spectrum of a photoinitiator.
Figure 6:
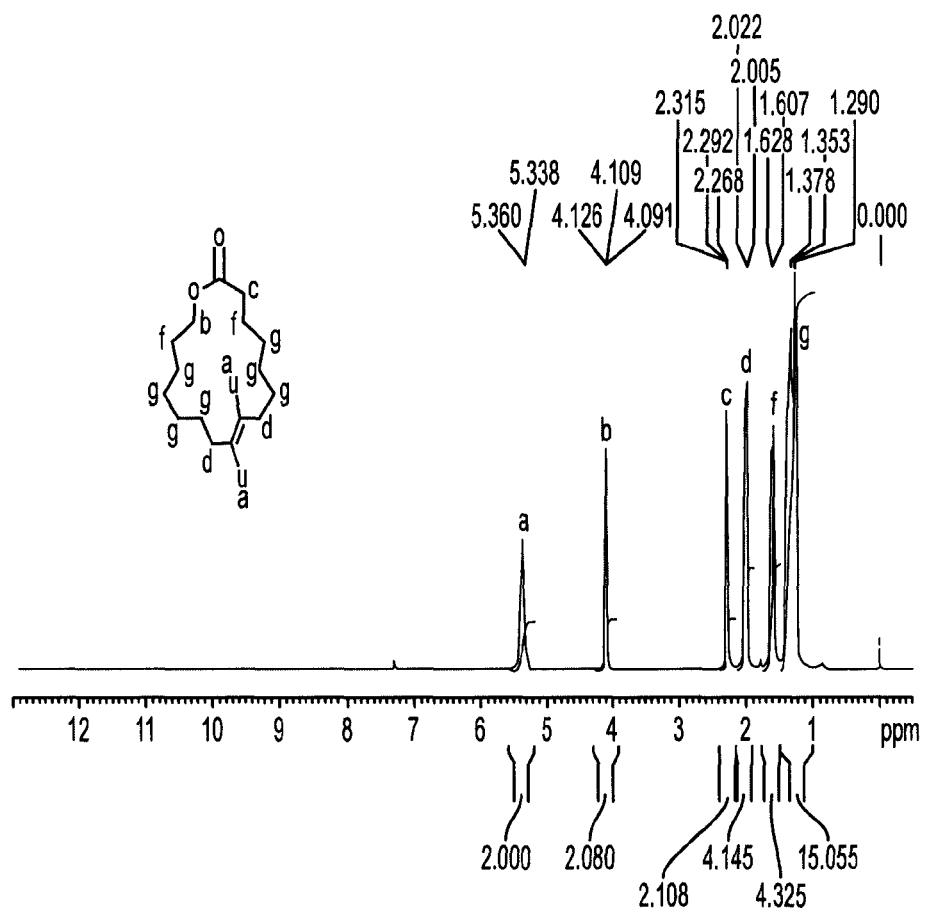
FIG. 6 is a 1H NMR spectrum of a lactone.
Figure 7:
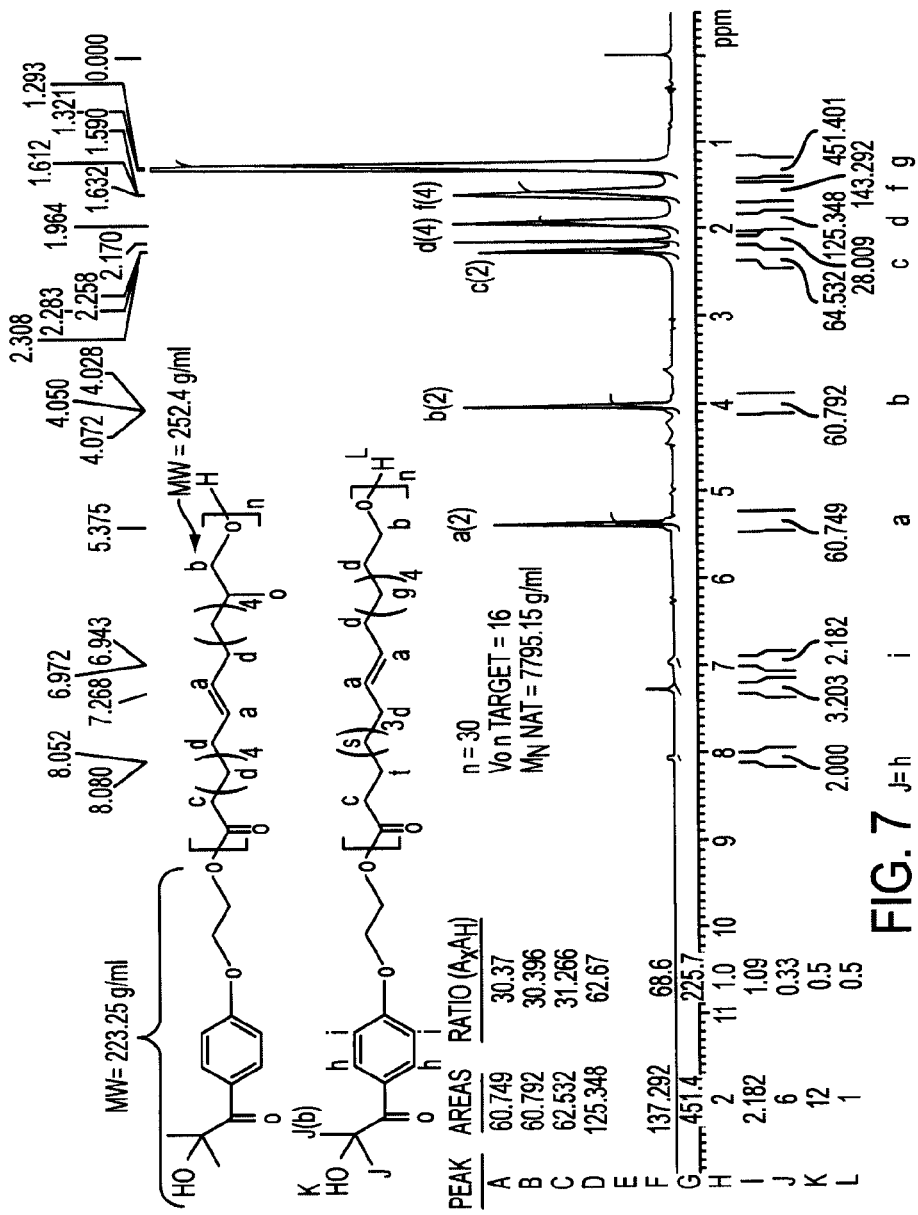
FIG. 7 is a 1H NMR spectrum of the reaction product of a photoinitiator and a lactone.

$^1$H NMR analysis of IRGACURE 2959, lactone (AMBRETTOLIDE) and the washed macro-photoinitiator is shown in FIGS. 5, 6 and 7, respectively. $^1$H NMR analysis of the washed macro-photoinitiator confirms the presence of photoinitiator. This analysis may also be used to quantify the ratio of monomer to photoinitiator, and reveals an average of approximately 30 monomer units per photoinitiator moiety. However, not all of the monomers are connected to a photoinitiator, as observed by GPC.

Example 2

The washed macro-photoinitiator from Example 1 was weighed into an aluminum pan (1.119 g) and melted to a temperature of 120° C. using a solids analyzer. The material turned from opaque white to clear once heated, as the crystalline domains in the polymer melted. The aluminum pan was fixed to a tray which was passed three times under a UV lamp in order to homolytically cleave the photoinitiator tethered to the polyester and create free radical species that could cross-link the polyester via the unsaturation on the polyester back-bone. These unsaturated sights are shown as peaks a-a in FIG. 7.

Figure 8:
FIG. 8 is a photograph of a gel residue from the reaction of a photoinitiator and a lactone after soxhlet extraction and upon exposure to UV irradiation.

Once cooled, the material formed an opaque film indicating that the degree of cross-linking was small. This is expected because the unsaturated bond in the polyester is not very reactive to free radical polymerization. The pan, with its cured polyester content, was wrapped in a pre-weighed stainless steel mesh and extracted with toluene for 48 hours. The mesh was then dried and weighed. The resulting gel content, insoluble cross-linked fraction, was 2.3%. FIG. 8 is a picture of the gel on the stainless steel mesh. Example 2 demonstrates that the macro-photoinitiator is capable of curing unsaturated bonds in polymer resins, and that the photoinitiator bound to the polyester retains its functionality.

Example 3

The washed macro-photoinitiator of Example 1 was weighed into a 4 dram vial (0.107 g), and 0.933 g of SR9003 (propoxylated neopentyl glycol diacrylate, available from Sartomer Co.) were added. This vial is referred to as the "experimental vial".

A second vial was loaded with an equivalent amount of SR9003 only. This vial is referred to as the "control vial."

The experimental vial and the control vial were heated using a heat gun to a temperature of 120° C. so that the polyester macro-photoinitiator in the experimental vial would dissolve into the SR9003 to form a clear solution. The control vial was also heated to ensure that it had the same thermal history as the experimental vial.

The vial contents were emptied into separate pans. The experimental vial solution turned opaque when added to the experimental pan due to cooling and crystallization of the polyester domains within the SR9003 solution. The control vial solution remained liquid-like and clear in the control pan.

Both pans were then heated with a heat gun again in order to re-melt the crystalline domains in the experimental pan. Once hot, both pans were fixed to a metal tray and passed under a UV lamp three times. After the first pass under the UV lamp, the experimental sample containing the macro-photoinitiator cured to a solid clear film immediately. The experimental sample remained clear after cooling, indicating that the macro-photoinitiator was cured into the SR9003 acrylate base and thus incapable of reforming crystalline domains. In contrast, the control sample (SR9003 only) remained liquid even after a third pass under the UV lamp.

Figure 9:
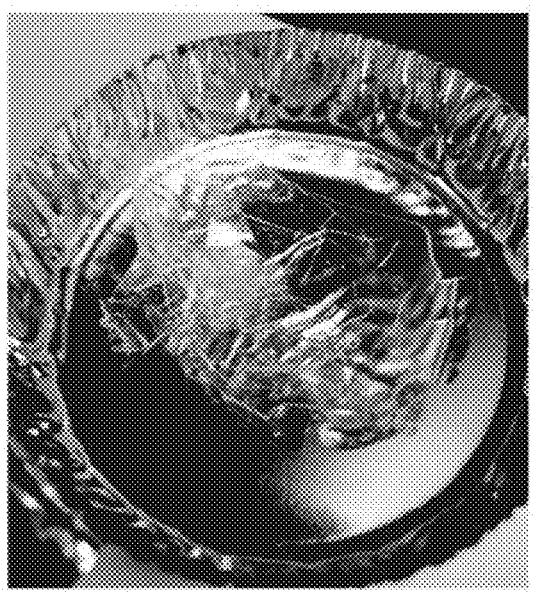
FIG. 9 is a photograph of a film comprising a macro-photoinitiator and curable monomer after exposure to UV irradiation.

The cured film was recovered from the experimental pan and soxhlet extracted in toluene for 60 hours. Analysis of the experimental film mass prior to and after extraction indicated that the film was 100% gel. There was no gel in the control pan, and the SR9003 solution remained liquid. FIG. 9 is a photograph of the experimental film after extraction.

Example 3 demonstrates that the macro-photoinitiator is capable of curing acrylate monomers, and that the bound photoinitiator retains its functionality after polymerization.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A process for producing a macro-photoinitiator via enzymatic polymerization, the process comprising:
   providing a reaction solution comprised of at least one monomer and at least one reactive photoinitiator having at least one reactive moiety reactive with the at least one monomer,
   contacting the reaction solution with at least one enzymatic catalyst, and
   heating to enzymatically polymerize the at least one monomer and form a polymeric product solution comprised of a macro-photoinitiator, wherein the macro-photoinitiator has the at least one reactive moiety of the at least one photoinitiator covalently bound to a polymer moiety formed from the at least one monomer, wherein the photoinitiator of the macro-photoinitiator includes an OH group, and wherein
   the at least one monomer is selected from the group consisting of oxacycloheptadec-10-en-2-one, pentadecalactone, pentadecenlactone, hexadecenlactone and caprolactone, cyclic diester lactide, butyrolactone, propyl malolactone, propiolactone, 1,4-dioxan-2-one, valerolactone, and mixtures thereof.

2. The process of claim 1, wherein the at least one enzymatic catalyst is selected from the group consisting of lipase PA, lipase PC, lipase PF, lipase A, lipase CA, lipase B, lipase CC, lipase K, lipase MM, cutinase, porcine lipase and mixtures thereof.

3. The process of claim 2, wherein the at least one enzymatic catalyst is *candita antartica* lipase B.

4. The process of claim 1, wherein the heating comprises heating the reaction solution while in contact with the enzymatic catalyst to a temperature of from about 40° C. to about 100° C.

5. The process of claim 1, wherein the at least one monomer comprises from about 5 to about 25 carbon atoms.

6. The process of claim 5, wherein the at least one monomer comprises a cyclic ester.

7. The process of claim 1, wherein the at least one reactive photoinitiator has a formula HO—R-photoinitiator, wherein R is a straight or branched carbon atom chain, saturated or unsaturated, having from 1 to 30 carbon atoms and optionally with one or more carbon atoms substituted with a heteroatom.

8. The process of claim 1, wherein the at least one photoinitiator is 1-[4-(2-hydroxyethoxy)-phenyl]-2-hydroxy-2-methyl-1-propane-1-one.

9. The process of claim 1, wherein the enzymatic catalyst is immobilized in a packed bed of a reactor, and wherein the contacting with the enzymatic catalyst comprises feeding the reaction solution through the packed bed reactor.

10. The process of claim 1, wherein the contacting comprises including the enzymatic catalyst in the reaction solution.

11. A macro-photoinitiator having a formula photoinitiator-R—O-polymer, wherein
   R is a straight or branched carbon atom chain, saturated or unsaturated, having from 1 to 30 carbon atoms and optionally with one or more carbon atoms substituted with a heteroatom;
   the photoinitiator of the macro-photoinitiator includes an OH group; and
   the polymer is comprised of n linked monomer units, n being an integer of from 3 to 200, wherein
      the monomer units are derived from one or more of oxacycloheptadec-10-en-2-one, pentadecalactone, pentadecenlactone, hexadecenlactone and caprolactone, cyclic diester lactide, butyrolactone, propyl malolactone, propiolactone, 1,4-dioxan-2-one, and valerolactone.

12. The macro-photoinitiator of claim 11, wherein the photoinitiator is 1-[4-(2-hydroxyethoxy)-phenyl]-2-hydroxy-2-methyl-1-propane-1-one.

13. A curable composition comprising at least one UV curable matrix material and at least one macro-photoinitiator, wherein the at least one macro-photoinitiator contains a polymer comprised of n linked monomer units, n being an integer of from 3 to 200, wherein the monomer units are derived from one or more of oxacycloheptadec-10-en-2-one, pentadecalactone, pentadecenlactone, hexadecenlactone and caprolactone, cyclic diester lactide, butyrolactone, propyl malolactone, propiolactone, 1,4-dioxan-2-one, and valerolactone.

14. The curable composition according to claim 13, wherein the curable matrix material is a curable monomer, macromer, oligomer and/or polymer of propoxylated neopentyl glycol diacrylate, styrene, alpha-methylstyrene, substituted styrene, vinyl esters, vinyl ethers, N-vinyl-2-pyrrolidone, (meth)acrylamide, N-substituted (meth)acrylamide, octyl (meth)acrylate, nonylphenol ethoxylate (meth)acrylate, isononyl (meth)acrylate, isobornyl (meth)acrylate, 2-(2-ethoxyethoxy)ethyl (meth)acrylate, 2-ethylhexyl (meth)acrylate, lauryl (meth)acrylate, β-carboxyethyl (meth)acrylate, isobutyl (meth)acrylate, cycloaliphatic epoxide, α-epoxide, 2-hydroxyethyl (meth)acrylate, (meth)acrylonitrile, maleic anhydride, itaconic acid, isodecyl (meth)acrylate, dodecyl (meth)acrylate, n-butyl (meth)acrylate, methyl (meth)acrylate, hexyl (meth)acrylate, (meth)acrylic acid, N-vinylcaprolactam, stearyl (meth)acrylate, hydroxy functional caprolactone ester (meth)acrylate, isooctyl (meth)acrylate, hydroxyethyl (meth)acrylate, hydroxymethyl (meth)acrylate, hydroxypropyl (meth)acrylate, hydroxyisopropyl (meth)acrylate, hydroxybutyl (meth)acrylate, hydroxyisobutyl (meth)acrylate, tetrahydrofurfuryl (meth)acrylate, polyester and combinations thereof.

15. The curable composition of claim 13, wherein the macro-photoinitiator has a formula photoinitiator-R—O-polymer, wherein R is a straight or branched carbon atom chain, saturated or unsaturated, having from 1 to 30 carbon atoms and optionally with one or more carbon atoms substituted with a heteroatom.

16. The curable composition of claim 15, wherein the photoinitiator is 1-[4-(2-hydroxyethoxy)-phenyl]-2-hydroxy-2-methyl-1-propane-1-one.

17. The curable composition of claim 13, wherein the curable composition is a UV curable paint, a coating, a top coating, a clear coating, or an ink.

* * * * *